United States Patent
Zhang et al.

(10) Patent No.: US 10,710,940 B2
(45) Date of Patent: *Jul. 14, 2020

(54) TURBULENT FLUIDIZED-BED REACTOR, DEVICE, AND METHOD USING OXYGEN-CONTAINING COMPOUND FOR MANUFACTURING PROPENE AND C4 HYDROCARBON

(71) Applicant: DALIAN INSTITUTE OF CHEMICAL PHYSICS, CHINESE ACADEMY OF SCIENCES, Dalian (CN)

(72) Inventors: Tao Zhang, Dalian (CN); Mao Ye, Dalian (CN); Changqing He, Dalian (CN); Jinling Zhang, Dalian (CN); Xiangao Wang, Dalian (CN); Hailong Tang, Dalian (CN); Jinming Jia, Dalian (CN); Yinfeng Zhao, Dalian (CN); Zhongmin Liu, Dalian (CN)

(73) Assignee: DALIAN INSTITUTE OF CHEMICAL PHYSICS, CHINESE ACADEMY OF SCIENCES, Dalian (CN)

( * ) Notice: Subject to any disclaimer, the term of this patent is extended or adjusted under 35 U.S.C. 154(b) by 0 days.

This patent is subject to a terminal disclaimer.

(21) Appl. No.: 16/342,587

(22) PCT Filed: Oct. 19, 2016

(86) PCT No.: PCT/CN2016/102560
§ 371 (c)(1),
(2) Date: Apr. 17, 2019

(87) PCT Pub. No.: WO2018/072139
PCT Pub. Date: Apr. 26, 2018

(65) Prior Publication Data
US 2019/0256439 A1    Aug. 22, 2019

(51) Int. Cl.
*C07C 1/20* (2006.01)
*B01J 8/00* (2006.01)
(Continued)

(52) U.S. Cl.
CPC ............... *C07C 1/20* (2013.01); *B01J 8/0025* (2013.01); *B01J 8/0055* (2013.01); *B01J 8/1827* (2013.01);
(Continued)

(58) Field of Classification Search
CPC ... C07C 1/20; C07C 11/02; C07C 11/06; C07C 4/06; C07C 11/04; C07C 2529/85;
(Continued)

(56) References Cited

U.S. PATENT DOCUMENTS

| 9,233,350 B2 | 1/2016 | Qi et al. |
| 2014/0148631 A1 | 5/2014 | Chewter et al. |

FOREIGN PATENT DOCUMENTS

| CN | 101239873 A | 8/2008 |
| CN | 101239874 A | 8/2008 |

(Continued)

OTHER PUBLICATIONS

International Search Report dated Jul. 19, 2017 in corresponding International application No. PCT/CN2016/102560; 6 pages.
(Continued)

*Primary Examiner* — Sharon Pregler
(74) *Attorney, Agent, or Firm* — Maier & Maier, PLLC

(57) ABSTRACT

A turbulent fluidized-bed reactor, device and method for preparing propylene and C4 hydrocarbons from oxygen-containing compounds. The device includes the turbulent fluidized-bed reactor and a fluidized-bed regenerator for regenerating a catalyst. The method includes: a) feeding a raw material containing the oxygen-containing compounds from n reactor feed distributors to a reaction zone of the (Continued)

turbulent fluidized-bed reactor, and contacting the raw material with a catalyst, to generate a stream containing target product and a spent catalyst containing carbon; b) sending the stream discharged into a product separation system, obtaining propylene, C4 hydrocarbons, light fractions and the like after separation, returning 70 wt. % or more of the light fractions to the reaction zone of the turbulent fluidized-bed reactor from the reactor feed distributor, and reacting ethylene and the oxygen-containing compounds to perform an alkylation reaction in presence of the catalyst, to produce products of propylene and the like.

20 Claims, 1 Drawing Sheet

(51) Int. Cl.
*B01J 8/18* (2006.01)
*B01J 8/26* (2006.01)
*C07C 11/04* (2006.01)
*C07C 11/06* (2006.01)

(52) U.S. Cl.
CPC ........... *B01J 8/1836* (2013.01); *B01J 8/1872* (2013.01); *B01J 8/1881* (2013.01); *B01J 8/26* (2013.01); *C07C 11/04* (2013.01); *C07C 11/06* (2013.01); *B01J 2208/00769* (2013.01); *B01J 2208/00938* (2013.01); *B01J 2208/00991* (2013.01); *Y02P 20/584* (2015.11); *Y02P 30/42* (2015.11)

(58) Field of Classification Search
CPC .. C07C 6/04; C07C 11/08; C07C 1/26; C07C 1/322; C07C 1/323; C07C 11/20; C07C 2529/035; B01J 29/85; B01J 29/90; B01J 29/84; B01J 38/12
See application file for complete search history.

(56) References Cited

FOREIGN PATENT DOCUMENTS

| | | |
|---|---|---|
| CN | 101177374 B | 6/2011 |
| CN | 102463086 A | 5/2012 |
| CN | 104098429 A | 10/2014 |
| CN | 104672044 A | 6/2015 |
| CN | 104672045 A | 6/2015 |
| KR | 10-2016-0093676 A | 8/2016 |
| WO | 01/62689 A1 | 8/2001 |
| WO | 2004/018089 A1 | 3/2004 |
| WO | 2009/065870 A1 | 5/2009 |

OTHER PUBLICATIONS

Extended European Search Report dated Feb. 26, 2020, including the Supplementary European Search Report and the European Search Opinion, in connection with corresponding EP Application No. 16919195.4 (8 pgs.).

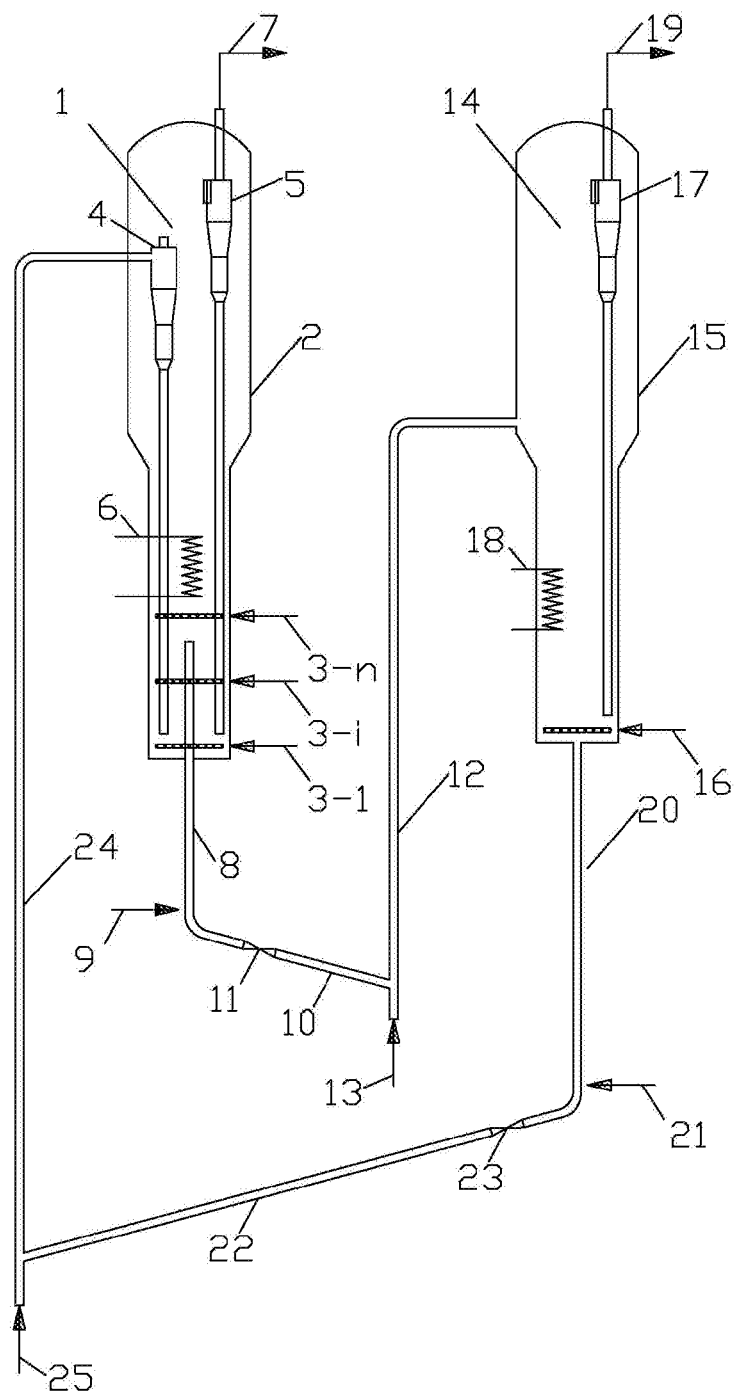

TURBULENT FLUIDIZED-BED REACTOR, DEVICE, AND METHOD USING OXYGEN-CONTAINING COMPOUND FOR MANUFACTURING PROPENE AND C4 HYDROCARBON

FIELD

The present invention refers to the field of chemical catalysis, in particular to a method and device for preparing propylene and C4 hydrocarbons from oxygen-containing compounds.

BACKGROUND

Propylene and butadiene are important chemical raw materials, which are usually obtained from naphtha cracking and steam cracking. The main sources of propylene are co-production of ethylene with propylene and by-product of refinery. The main source of butadiene is the further processing of C4 by-product produced in ethylene cracking process. In recent years, the technologies of methanol to olefin (MTO), methanol to propylene (MTP), ethane dehydrogenation to ethylene and propane dehydrogenation to propylene have been rapidly developed. There is an obvious tendency of raw material lightening in global olefin production, which will lead to the shortage of C4 resources. Therefore, it is necessary to develop a process that can produce propylene and C4 olefins with a high selectivity to meet market demand The fixed-bed methanol-to-olefin technology (WO2004/018089) was developed by LURGI AG in Germany. The technology utilized a ZSM-5 molecular sieve catalyst from Sud-Chemie AG to carry out methanol-to-olefin reaction in a fixed-bed reactor. The selectivity of propylene was close to 70%, and the by-products were ethylene, liquefied petroleum gas and gasoline.

The DMTO technology developed by Dalian Institute of Chemical Physics used a SAPO molecular sieve as catalyst, a dense-phase circulating fluidized-bed reactor and a methanol aqueous solution as raw material. The yield of ethylene and propylene in the product was about 80%, and more than 10% of C4 hydrocarbons were yielded as by-products.

Patent CN104098429A discloses a method of preparing propylene and C4 hydrocarbons from methanol in a circulating fluidized-bed using a ZSM-5 catalyst. The process features are that the raw material methanol and most of C1, C2 and C5 hydrocarbons in the product are entered into the circulating fluidized-bed reactor together, and propylene, C4 hydrocarbons, hydrocarbons of C6 and above and by-products are retrieved as final products.

Patent CN101177374B discloses a method for preparing olefins from methanol or dimethyl ether. The method includes the conversion of methanol or dimethyl ether, the alkylation of ethylene and methanol, and the catalytic cracking of components heavier than C4. Catalyst 1 is used for the methanol or dimethyl ether conversion and the ethylene and methanol alkylation in one reactor, and catalyst 2 is used for the catalytic cracking of components heavier than C4 in another reactor.

The methods disclosed in patents CN104098429A and CN101177374B share a common feature, that is, the selectivity of target products (propylene and C4) is increased through the recycling of light fractions (hydrocarbons with a carbon number of no more than 2). The alkylation of ethylene with methanol is the main reaction in the recycling reaction of the light fractions mentioned above.

The acidic molecular sieve catalysts can be used in both MTO reaction and alkylation of olefins. However, the rate of the MTO reaction is much higher than that of the alkylation of olefins. We have found that a fresh SAPO catalyst has a high activity, which is more beneficial to the alkylation of olefins. After a carbon deposition of catalyst, the reaction rate of alkylation of olefins will decrease rapidly.

Methanol is not only the raw material for the alkylation of olefins, but also the raw material for the MTO reaction. Therefore, the alkylation of olefins is necessarily accompanied by the MTO reaction. The MTO reaction will lead to a carbon deposition and lower activity of catalyst, which will hence inhibit the alkylation of olefins. An increase in the alkylation rate of olefins can reduce the content of light fractions in the product gas, and thus the unit volume production capacity of the reactor can be increased.

The methods disclosed in patents CN104098429A and CN101177374B do not refer to the reactor structure, nor do they clarify the flow modes of catalyst and raw material and the raw material distribution in the reactor. The method disclosed in patent CN101177374B uses a SAPO catalyst. The examples show that the mass ratio of methanol to light fractions is 1:10-20. Thus, it can be seen that the content of light fractions is very high and the unit volume production capacity of reactor is very low. A ZSM-5 catalyst is used in the method disclosed in patent CN104098429A. The content of hydrocarbons of C6 and above in the product is relatively high. The content of light fractions in the product gas is not disclosed in this method.

From the above analysis, it can be seen that the main reactions for the preparation of propylene and C4 hydrocarbons from methanol are the MTO reaction and the alkylation of olefins. Therefore, the key to improve the selectivity of propylene and C4 hydrocarbons lies in a catalyst design and a reactor design. Avoiding the inhibition of the MTO reaction to the alkylation of olefins through an optimization in the reactor design is one of the important methods to improve the economics of methanol to propylene and C4 hydrocarbons.

SUMMARY

In view of the problem of low reaction rate of ethylene alkylation, the present invention provides a new method and device for increasing the reaction rate of ethylene alkylation in the process of preparing propylene and C4 hydrocarbons from methanol. Being used in the production of propylene and C4 hydrocarbons from oxygen-containing compounds, the method has the advantages of high yield of propylene and C4 hydrocarbons and good process economics.

To achieve the above purposes, one aspect of the present invention provides a turbulent fluidized-bed reactor for preparing propylene and C4 hydrocarbons from oxygen-containing compounds. The turbulent fluidized-bed reactor comprises a reactor shell (2), n reactor feed distributors (3-1~3-n), a reactor gas-solid separator 1 (4), a reactor gas-solid separator 2 (5), a reactor heat extractor (6), a product gas outlet (7) and a reactor stripper (8), wherein the lower part of the turbulent fluidized-bed reactor (1) is a reaction zone, the upper part of the turbulent fluidized-bed reactor (1) is a settling zone, then reactor feed distributors (3-1~3-n) are disposed in the reaction zone from bottom to top, the reactor heat extractor (6) is disposed in the reaction zone, the reactor gas-solid separator 1 (4) and the reactor gas-solid separator 2 (5) are placed in the settling zone or outside the reactor shell (2), the reactor gas-solid separator 1 (4) is equipped with a regenerated catalyst inlet, the catalyst outlet of the reactor gas-solid separator 1 (4) is located at the bottom of the reaction zone, the gas outlet of the reactor gas-solid separator 1 (4) is located in the settling zone, the inlet of the reactor gas-solid separator 2 (5) is located in the settling zone, the catalyst outlet of the reactor gas-solid separator 2 (5) is placed in the reaction zone, the gas outlet of the reactor gas-solid separator 2 (5) is connected to the product gas outlet (7), the reactor stripper (8) passes through the reactor shell from outside to inside at the bottom of the turbulent fluidized-bed reactor and is opened in the reaction zone of the turbulent fluidized-bed reactor (1), a reactor stripping gas inlet (9) is arranged at the bottom of the reactor stripper (8), and a spent catalyst outlet is arranged at the bottom of the reactor stripper.

In a preferred embodiment, the n reactor feed distributors (3-1~3-$n$) of the turbulent fluidized-bed reactor (1) are disposed in the reaction zone from bottom to top, and $0<n<10$.

In a preferred embodiment, the horizontal height of opening of the reactor stripper (8) in the reactor shell (2) is higher than $\frac{1}{10}$ the height of the reaction zone, so as to avoid the direct entry of fresh catalyst into the reactor stripper.

In a preferred embodiment, the reactor gas-solid separator 1 (4) and the reactor gas-solid separator 2 (5) are cyclone separators.

The present invention further provides a device for preparing propylene and C4 hydrocarbons from oxygen-containing compounds, comprising the turbulent fluidized-bed reactor (1) described above and a fluidized-bed regenerator (14) for regenerating a catalyst.

In a preferred embodiment, the fluidized-bed regenerator (14) is a turbulent fluidized-bed regenerator.

In a preferred embodiment, the fluidized-bed regenerator (14) comprises a regenerator shell (15), a regenerator feed distributor (16), a regenerator gas-solid separator (17), a regenerator heat extractor (18), a flue gas outlet (19) and a regenerator stripper (20), wherein the lower part of the fluidized-bed regenerator (14) is a regeneration zone, the upper part of the fluidized-bed regenerator (14) is a settling zone, the regenerator feed distributor (16) is placed at the bottom of the regeneration zone, the regenerator heat extractor (18) is placed in the regeneration zone, the regenerator gas-solid separator (17) is placed in the settling zone or outside the regenerator shell (15), the inlet of the regenerator gas-solid separator (17) is disposed in the settling zone, the catalyst outlet of the regenerator gas-solid separator (17) is disposed in the regeneration zone, the gas outlet of the regenerator gas-solid separator (17) is connected to the flue gas outlet (19), and the inlet of the regenerator stripper (20) is connected to the bottom of the regenerator shell (15);

the spent catalyst outlet of the reactor stripper (8) is connected to the inlet of a inclined spent catalyst pipe (10), a spent catalyst sliding valve (11) is arranged in the inclined spent catalyst pipe (10), the outlet of the inclined spent catalyst pipe (10) is connected to the inlet of a spent catalyst lift pipe (12), the bottom of the spent catalyst lift pipe (12) is provided with a spent catalyst lifting gas inlet (13), and the outlet of the spent catalyst lift pipe (12) is connected to the settling zone of the fluidized-bed regenerator (14);

the bottom of the regenerator stripper (20) is provided with a regenerator stripping gas inlet (21), the bottom of the regenerator stripper (20) is connected to the inlet of a inclined regenerated catalyst pipe (22), a regenerated catalyst sliding valve (23) is arranged in the inclined regenerated catalyst pipe (22), the outlet of the inclined regenerated catalyst pipe (22) is connected to the inlet of a regenerated catalyst lift pipe (24), the bottom of the regenerated catalyst lift pipe (24) is provided with a regenerated catalyst lifting gas inlet (25), and the outlet of the regenerated catalyst lift pipe (24) is connected to the inlet of the reactor gas-solid separator 1 (4).

Another aspect of the present invention provides a method for preparing propylene and C4 hydrocarbons from oxygen-containing compounds, including:

feeding a raw material containing an oxygen-containing compound from n reactor feed distributors (3-1~3-$n$) to a reaction zone of a turbulent fluidized-bed reactor (1), and contacting the raw material with a catalyst, to generate a stream containing propylene and C4 hydrocarbons product and a spent catalyst containing carbon;

sending the stream discharged from the turbulent fluidized-bed reactor (1) containing propylene and C4 hydrocarbons product into a product separation system, obtaining propylene, C4 hydrocarbons, light fractions, propane and hydrocarbons with 5 or more carbons after separation, wherein the light fractions contain more than 90 wt % of ethylene and a small amount of methane, ethane, hydrogen, CO and $CO_2$, returning 70 wt. % or more of the light fractions to the reaction zone of the turbulent fluidized-bed reactor (1) from the reactor feed distributor (3-1) at the bottom-most of the turbulent fluidized-bed reactor (1), and reacting ethylene and the oxygen-containing compounds to perform an alkylation reaction in presence of the catalyst, to produce a product containing propylene;

regenerating the spent catalyst by a fluidized-bed regenerator (14), and after being gas-solid separated by a reactor gas-solid separator 1 (4), the regenerated catalyst is fed to the bottom of the reaction zone of the turbulent fluidized-bed reactor (1).

In a preferred embodiment, the method described in the present invention is carried out using the above-mentioned device for preparing propylene and C4 hydrocarbons from oxygen-containing compounds.

In a preferred embodiment, the spent catalyst passes through the reactor stripper (8), the inclined spent catalyst pipe (10), the spent catalyst sliding valve (11) and the spent catalyst lift pipe (12) into the settling zone of the fluidized-bed regenerator (14);

a regeneration medium enters the regeneration zone of the fluidized-bed regenerator (14) from the regenerator feed distributor (16) and reacts with the spent catalyst to perform calcination to produce a flue gas containing CO and $CO_2$ and the regenerated catalyst, and the flue gas is discharged after dust removal by the regenerator gas-solid separator (17);

the regenerated catalyst passes through the regenerator stripper (20), the inclined regenerated catalyst pipe (22), the regenerated catalyst sliding valve (23) and the regenerated catalyst lift pipe (24) into the inlet of the reactor gas-solid separator 1 (4), and after gas-solid separation, the regenerated catalyst enters the bottom of the reaction zone of the turbulent fluidized-bed reactor (1);

a reactor stripping gas enters the reactor stripper (8) via the reactor stripping gas inlet (9) and contacts countercurrent with the spent catalyst, and then enters the turbulent fluidized-bed reactor (1); a spent catalyst lifting gas enters the spent catalyst lift pipe (12) via the spent catalyst lifting gas inlet (13) and contacts cocurrent with the spent catalyst, and then enters the settling zone of the fluidized-bed regenerator (14);

a regenerator stripping gas enters the regenerator stripper (20) via the regenerator stripping gas inlet (21) and contacts countercurrent with the regenerated catalyst, and then enters the fluidized-bed regenerator (14); a regenerated catalyst lifting gas enters the regenerated catalyst lift pipe (24) via the regenerated catalyst lifting gas inlet (25) and contacts cocurrent with the regenerated catalyst, and then enters the inlet of the reactor gas-solid separator 1 (4).

The main characteristics of the turbulent fluidized-bed reactor in the present invention are that the light fractions enter from the reactor feed distributor at the bottom-most, the oxygen-containing compound enters from n reactor feed distributors respectively, and the regenerated catalyst directly enters the bottom of the reaction zone. On one hand, in the lower part of the reaction zone, the catalyst has a high activity, which is advantageous to the alkylation of ethylene, propylene and methanol; on the other hand, because of the multi-stage feeding of the oxygen-containing compounds, the case where most of the conversion reactions of the oxygen-containing compounds are completed in a small region of the lower part of the reaction zone is avoided, so that the concentration of the oxygen-containing compounds is more uniform in most of the reaction zone, weakening the inhibition of MTO reaction to the alkylation of olefins. Therefore, the turbulent fluidized-bed reactor in the present invention can effectively improve the alkylation reaction rate of olefins, and the unit volume production capacity of the reactor is high.

In the method for preparing propylene and C4 hydrocarbons from oxygen-containing compounds of the present invention, the MTO reaction produces ethylene, propylene, and the like, and the alkylation of olefins consumes ethylene, propylene, and the like. Since the reaction rate of ethylene alkylation is high, the content of light fractions in the product gas is low, and the circulating amount of the light fractions is low. In the method of the present invention, the circulating amount of the light fractions is 5-40 wt. % of the feeding amount of the oxygen-containing compound.

In the method of the present invention, 70 wt. % or more of the light fractions are circulated in the system, and the release rate of the light fractions affects the composition of the product gas in the equilibrium state. In the equilibrium state, the product gas consists of 20-50 wt. % propylene, 15-40 wt. % C4 hydrocarbons, 10-45 wt. % light fractions, 0-5 wt. % propane and 5-20 wt. % hydrocarbons with 5 or more carbons. The light fractions contain more than 90 wt. %, e.g. >95 wt. % ethylene, and other components include methane, ethane, hydrogen, CO and $CO_2$.

In a preferred embodiment, the catalyst contains a SAPO molecular sieve, and the catalyst simultaneously has the functions of catalyzing methanol to olefins and alkylation of olefins.

In a preferred embodiment, the carbon content of the regenerated catalyst is less than 2 wt. %, and further preferably, the carbon content of the regenerated catalyst is less than 0.5 wt. %.

In a preferred embodiment, the carbon content of the spent catalyst is 5-12 wt. %, and further preferably, the carbon content of the spent catalyst is 5-10 wt. %.

In a preferred embodiment, the reaction conditions in the reaction zone of the turbulent fluidized-bed reactor (1) are as follows: the apparent linear velocity of gas is in a range from 0.1 m/s to 2 m/s, the reaction temperature is in a range from 300° C. to 550° C., the reaction pressure is in a range from 100 kPa to 500 kPa, and the bed density is in a range from 200 kg/m$^3$ to 1200 kg/m$^3$.

In a preferred embodiment, the reaction conditions in the regeneration zone of the fluidized-bed regenerator (14) are as follows: the apparent linear velocity of gas is in a range from 0.1 m/s to 2 m/s, the regeneration temperature is in a range from 500° C. to 750° C., the regeneration pressure is in a range from 100 kPa to 500 kPa, and the bed density is in a range from 200 kg/m$^3$ to 1200 kg/m$^3$.

In a preferred embodiment, the oxygen-containing compound is methanol and/or dimethyl ether; the regeneration medium is any one of air, oxygen-poor air or water vapor or a mixture thereof; the reactor stripping gas, the regenerator stripping gas, the spent catalyst lifting gas and the regenerated catalyst lifting gas are water vapor or nitrogen.

BRIEF DESCRIPTION OF THE FIGURES

FIG. 1 is a schematic diagram of a device for preparing propylene and C4 hydrocarbons from oxygen-containing compounds according to an embodiment of the present invention.

The Reference Numerals in the FIGURE are Listed as Follows:

1—turbulent fluidized-bed reactor; 2—reactor shell; 3—reactor feed distributors (3-1~3-n); 4—reactor gas-solid separator 1; 5—reactor gas-solid separator 2; 6—reactor heat extractor; 7—product gas outlet; 8—reactor stripper; 9—reactor stripping gas inlet; 10—inclined spent catalyst pipe; 11—spent catalyst sliding valve; 12—spent catalyst lift pipe; 13—spent catalyst lifting gas inlet; 14—fluidized-bed regenerator; 15—regenerator shell; 16—regenerator feed distributor; 17—regenerator gas-solid separator; 18—regenerator heat extractor; 19—flue gas outlet; 20—regenerator stripper; 21—regenerator stripping gas inlet; 22—inclined regenerated catalyst pipe; 23—regenerated catalyst sliding valve; 24—regenerated catalyst lift pipe; 25—regenerated catalyst lifting gas inlet.

DETAILED DESCRIPTION

In a specific embodiment, the schematic diagram of the device according to the present invention for preparing propylene and C4 hydrocarbons from oxygen-containing compounds is shown in FIG. 1, which comprises:

a) a turbulent fluidized-bed reactor (1), which comprises a reactor shell (2), n reactor feed distributors (3-1~3-n), a reactor gas-solid separator 1 (4), a reactor gas-solid separator 2 (5), a reactor heat extractor (6), a product gas outlet (7) and a reactor stripper (8), wherein the lower part of the turbulent fluidized-bed reactor (1) is a reaction zone, the upper part of the turbulent fluidized-bed reactor (1) is a settling zone, then reactor feed distributors (3-1~3-n) are arranged from bottom to top in the reaction zone and 0<n<10, the reactor heat extractor (6) is disposed in the reaction zone, the reactor gas-solid separator 1 (4) and the reactor gas-solid separator 2 (5) are placed in the settling zone or outside the reactor shell (2), the inlet of the reactor gas-solid separator 1 (4) is connected to a regenerated catalyst lift pipe (24), the catalyst outlet of the reactor gas-solid separator 1 (4) is located at the bottom of the reaction zone, the gas outlet of the reactor gas-solid separator 1 (4) is located in the settling zone, the inlet of the reactor gas-solid separator 2 (5) is located in the settling zone, the catalyst outlet of the reactor gas-solid separator 2 (5) is located in the reaction zone, the gas outlet of the reactor gas-solid separator 2 (5) is connected to the product gas outlet (7), and the inlet of the reactor stripper (8) is in the reaction zone of the turbulent fluidized-bed reactor (1), with the horizontal height higher than $\frac{1}{10}$ that of the reaction zone;

b) a fluidized-bed regenerator (14), which comprises a regenerator shell (15), a regenerator feed distributor (16), a regenerator gas-solid separator (17), a regenerator heat extractor (18), a flue gas outlet (19) and a regenerator stripper (20), wherein the lower part of the fluidized-bed regenerator (14) is a regeneration zone, the upper part of the fluidized-bed regenerator (14) is a settling zone, the regenerator feed distributor (16) is placed at the bottom of the regeneration zone, the regenerator heat extractor (18) is placed in the regeneration zone, the regenerator gas-solid separator (17) is placed in the settling zone or outside the regenerator shell (15), the inlet of the regenerator gas-solid separator (17) is placed in the settling zone, the catalyst outlet of the regenerator gas-solid separator (17) is placed in the regeneration zone, the gas outlet of the regenerator gas-solid separator (17) is connected to the flue gas outlet (19), and the inlet of the regenerator stripper (20) is connected to the bottom of the regenerator shell (15);

c) the bottom of the reactor stripper (8) is provided with a reactor stripping gas inlet (9), the bottom of the reactor stripper (8) is connected to the inlet of a inclined spent catalyst pipe (10), a spent catalyst sliding valve (11) is arranged in the inclined spent catalyst pipe (10), the outlet of the inclined spent catalyst pipe (10) is connected to the inlet of a spent catalyst lift pipe (12), the bottom of the spent catalyst lift pipe (12) is provided with a spent catalyst lifting gas inlet (13), and the outlet of the spent catalyst lift pipe (12) is connected to the settling zone of the fluidized-bed regenerator (14);

d) the bottom of the regenerator stripper (20) is provided with a regenerator stripping gas inlet (21), the bottom of the regenerator stripper (20) is connected to the inlet of a inclined regenerated catalyst pipe (22), a regenerated catalyst sliding valve (23) is arranged in the inclined regenerated catalyst pipe (22), the outlet of the inclined regenerated catalyst pipe (22) is connected to the inlet of the regenerated catalyst lift pipe (24), the bottom of the regenerated catalyst lift pipe (24) is provided with a regenerated catalyst lifting gas inlet (25), and the outlet of the regenerated catalyst lift pipe (24) is connected to the inlet of the reactor gas-solid separator 1 (4).

In the above embodiment, the fluidized-bed regenerator (14) may be a turbulent fluidized-bed regenerator; the reactor gas-solid separator 1 (4), the reactor gas-solid separator 2 (5) and the regenerator gas-solid separator (17) may be cyclone separators.

In a specific embodiment, the method according to the present invention for preparing propylene and C4 hydrocarbons from oxygen-containing compounds includes the following steps:

a) feeding a raw material containing oxygen-containing compounds into the reaction zone of the turbulent fluidized-bed reactor (1) from the n reactor feed distributors (3-1~3-n), and contacting the raw material with a catalyst, to generate a stream containing propylene and C4 hydrocarbons product and a spent catalyst containing carbon;

b) sending the stream discharged from the turbulent fluidized-bed reactor (1) containing propylene and C4 hydrocarbons product into the product separation system, obtaining propylene, C4 hydrocarbons, light fractions, propane and hydrocarbons with 5 or more carbons after separation, wherein the light fractions are mainly ethylene with a small amount of methane, ethane, hydrogen, CO and $CO_2$, returning 70 wt. % or more of the light fractions to the reaction zone of the turbulent fluidized-bed reactor (1) from the reactor feed distributor (3-1) at the bottom-most of the turbulent fluidized-bed reactor (1), and reacting ethylene and the oxygen-containing compounds to perform an alkylation reaction in presence of the catalyst to produce a product containing propylene, with less than 30 wt. % of the light fractions being retrieved as a by-product;

c) the spent catalyst passes through the reactor stripper (8), the inclined spent catalyst pipe (10), the spent slide valve (11) and the spent catalyst lift pipe (12) into the settling zone of the fluidized-bed regenerator (14);

d) a regeneration medium enters the regeneration zone of the fluidized-bed regenerator (14) from the regenerator feed distributor (16), the regeneration medium reacts with the spent catalyst to perform calcination to produce a flue gas containing CO and $CO_2$ and a regenerated catalyst, and the flue gas is discharged after dust removal by the regenerator gas-solid separator (17);

e) the regenerated catalyst passes through the regenerator stripper (20), the inclined regenerated catalyst pipe (22), the regenerated catalyst sliding valve (23) and the regenerated catalyst lift pipe (24) into the inlet of the reactor gas-solid separator 1 (4), and after gas-solid separation, the regenerated catalyst enters the bottom of the reaction zone of the turbulent fluidized-bed reactor (1);

f) a reactor stripping gas enters the reactor stripper (8) via the reactor stripping gas inlet (9) and contacts countercurrent with the spent catalyst, and then enters the turbulent fluidized-bed reactor (1); a spent catalyst lifting gas enters the spent catalyst lift pipe (12) via the spent catalyst lifting gas inlet (13) and contacts cocurrent with the spent catalyst, and then enters the settling zone of the fluidized-bed regenerator (14);

g) a regenerator stripping gas enters the regenerator stripper (20) via the regenerator stripping gas inlet (21) and contacts countercurrent with the regenerated catalyst, and then enters the fluidized-bed regenerator (14); a regenerated catalyst lifting gas enters the regenerated catalyst lift pipe (24) via the regenerated catalyst lifting gas inlet (25) and contacts cocurrent with the regenerated catalyst, and then enters the inlet of the reactor gas-solid separator 1 (4).

In order to better illustrate the present invention and facilitate the understanding of the technical scheme of the present invention, comparative examples and representative but non-restrictive examples of the present invention are listed as follows:

EXAMPLE 1

The present example is a comparative example. The device shown in FIG. 1 is used, but the turbulent fluidized-bed reactor (1) does not contain the reactor gas-solid separator 1 (4), and the regenerated catalyst lift pipe (24) is directly connected to the settling zone of the turbulent fluidized-bed reactor (1).

The turbulent fluidized-bed reactor (1) contains three reactor feed distributors (3-1-3-3), the reactor gas-solid separator 1 (4) is placed outside the reactor shell (2), and the horizontal height of the inlet of the reactor stripper (8) is at ½ height of the reaction zone. The reaction conditions in the reaction zone of the turbulent fluidized-bed reactor (1) are as follows: the apparent linear velocity of gas is about 1.0 m/s, the reaction temperature is about 450° C., the reaction pressure is about 150 kPa, and the bed density is about 350 $kg/m^3$.

The reaction conditions in the regeneration zone of the fluidized-bed regenerator (14) are as follows: the apparent linear velocity of gas is about 1.0 m/s, the regeneration temperature is about 650° C., the regeneration pressure is about 150 kPa, and the bed density is about 350 $kg/m^3$.

The catalyst contains a SAPO molecular sieve. The carbon content of the spent catalyst is about 7%, and the carbon content of the regenerated catalyst is about 0.2 wt. %.

The oxygen-containing compound is methanol, and the regeneration medium is air; the reactor stripping gas, the regenerator stripping gas, the spent catalyst lifting gas and the regenerated catalyst lifting gas are water vapor.

The circulating amount of the light fractions is 20 wt. % of the feeding amount of methanol, and 83 wt. % of the light fractions are circulated in the system.

The composition of the product gas discharged from the turbulent fluidized-bed reactor (1) is: 34 wt. % propylene, 20 wt. % C4 hydrocarbons, 35 wt. % light fractions, 1 wt. % propane and 10 wt. % hydrocarbons with 5 or more carbons. The light fractions contain 99 wt. % ethylene and 1 wt. % methane, ethane, hydrogen, CO, $CO_2$, and the like.

The composition of the product gas discharged from the separation system is: 48 wt. % propylene, 28 wt. % C4 hydrocarbons, 9 wt. % light fractions, 1 wt. % propane and 14 wt. % hydrocarbons with 5 or more carbons.

EXAMPLE 2

The device shown in FIG. 1 is used. The turbulent fluidized-bed reactor (1) contains three reactor feed distributors (3-1~3-3), the reactor gas-solid separator 1 (4) is placed outside the reactor shell (2), and the horizontal height of the inlet of the reactor stripper (8) is at ½ height of the reaction zone. The reaction conditions in the reaction zone of the turbulent fluidized-bed reactor (1) are as follows: the apparent linear velocity of gas is about 1.0 m/s, the reaction temperature is about 450° C., the reaction pressure is about 150 kPa, and the bed density is about 350 kg/m³.

The reaction conditions in the regeneration zone of the fluidized-bed regenerator (14) are as follows: the apparent linear velocity of gas is about 1.0 m/s, the regeneration temperature is about 650° C., the regeneration pressure is about 150 kPa, and the bed density is about 350 kg/m³.

The catalyst contains a SAPO molecular sieve. The carbon content of the spent catalyst is about 7%, and the carbon content of the regenerated catalyst is about 0.2 wt. %.

The oxygen-containing compound is methanol, and the regeneration medium is air; the reactor stripping gas, the regenerator stripping gas, the spent catalyst lifting gas and the regenerated catalyst lifting gas are water vapor.

The circulating amount of the light fractions is 20 wt. % of the feeding amount of methanol, and 98 wt. % of the light fractions are circulated in the system.

The composition of the product gas discharged from the turbulent fluidized-bed reactor (1) is: 32 wt. % propylene, 24 wt. % C4 hydrocarbons, 31 wt. % light fractions, 2 wt. % propane and 11 wt. % hydrocarbons with 5 or more carbons. The light fractions contain 97 wt. % ethylene and 3 wt. % methane, ethane, hydrogen, CO, $CO_2$, and the like.

The composition of the product gas discharged from the separation system is: 46 wt. % propylene, 34 wt. % C4 hydrocarbons, 1 wt. % light fractions, 3 wt. % propane and 16 wt. % hydrocarbons with 5 or more carbons.

The present example is different from Example 1 (comparative example) merely in that the regenerated catalyst enters the bottom of the turbulent fluidized-bed reactor and contacts firstly with the light fractions, while in Example 1, the regenerated catalyst enters the settling zone of the turbulent fluidized-bed reactor. Comparing the present example with Example 1, it can be seen that the conversion rate of light fractions can be greatly improved when the catalyst is contacted firstly with the light fractions. The light fractions discharged from the separation system in present example is only 11% of that in the comparative example. Therefore, the device of the present invention effectively improves the reaction rate of ethylene alkylation.

EXAMPLE 3

The device shown in FIG. 1 is used. The turbulent fluidized-bed reactor (1) contains four reactor feed distributors (3-1~3-4), the reactor gas-solid separator 1 (4) is placed in the settling zone, and the horizontal height of the inlet of the reactor stripper (8) is at ¾ height of the reaction zone. The reaction conditions in the reaction zone of the turbulent fluidized-bed reactor (1) are as follows: the apparent linear velocity of gas is about 1.2 m/s, the reaction temperature is about 360° C., the reaction pressure is about 200 kPa, and the bed density is about 300 kg/m³.

The reaction conditions in the regeneration zone of the fluidized-bed regenerator (14) are as follows: the apparent linear velocity of gas is about 1.2 m/s, the regeneration temperature is about 700° C., the regeneration pressure is about 200 kPa, and the bed density is about 300 kg/m³.

The catalyst contains a SAPO molecular sieve. The carbon content of the spent catalyst is about 8%, and the carbon content of the regenerated catalyst is about 0.1 wt. %.

The oxygen-containing compound is methanol, and the regeneration medium is air; the reactor stripping gas, the regenerator stripping gas, the spent catalyst lifting gas and the regenerated catalyst lifting gas are water vapor.

The circulating amount of the light fractions is 16 wt. % of the feeding amount of methanol, and 90 wt. % of the light fractions are circulated in the system.

The composition of the product gas discharged from the turbulent fluidized-bed reactor (1) is: 34 wt. % propylene, 25 wtt. % C4 hydrocarbons, 29 wt. % light fractions, 2 wt. % propane and 10 wt. % hydrocarbons with 5 or more carbons. The light fractions contain 98 wt. % ethylene and 2 wt. % methane, ethane, hydrogen, CO, $CO_2$, and the like.

The composition of the product gas discharged from the separation system is: 46 wt. % propylene, 34 wt. % C4 hydrocarbons, 4 wt. % light fractions, 3 wt. % propane and 13 wt. % hydrocarbons with 5 or more carbons.

EXAMPLE 4

The device shown in FIG. 1 is used. The turbulent fluidized-bed reactor (1) contains six reactor feed distributors (3-1~3-6), the reactor gas-solid separator 1 (4) is placed in the settling zone, and the horizontal height of the inlet of the reactor stripper (8) is at ⅚ height of the reaction zone. The reaction conditions in the reaction zone of the turbulent fluidized-bed reactor (1) are as follows: the apparent linear velocity of gas is about 1.5 m/s, the reaction temperature is about 420° C., the reaction pressure is about 250 kPa, and the bed density is about 250 kg/m³.

The reaction conditions in the regeneration zone of the fluidized-bed regenerator (14) are as follows: the apparent linear velocity of gas is about 1.5 m/s, the regeneration temperature is about 700° C., the regeneration pressure is about 250 kPa, and the bed density is about 250 kg/m³.

The catalyst contains a SAPO molecular sieve. The carbon content of the spent catalyst is about 9%, and the carbon content of the regenerated catalyst is about 0.05 wt. %.

The oxygen-containing compound is dimethyl ether, and the regeneration medium is oxygen-poor air; the reactor stripping gas, the regenerator stripping gas, the spent catalyst lifting gas and the regenerated catalyst lifting gas are nitrogen.

The circulating amount of the light fractions is 14 wt. % of the feeding amount of dimethyl ether, and 85 wt. % of the light fractions are circulated in the system.

The composition of the product gas discharged from the turbulent fluidized-bed reactor (1) is: 38 wt. % propylene, 30 wt. % C4 hydrocarbons, 21 wt. % light fractions, 2 wt. % propane and 9 wt. % hydrocarbons with 5 or more carbons. The light fractions contain 98 wt. % ethylene and 2 wt. % methane, ethane, hydrogen, CO, $CO_2$, and the like.

The composition of the product gas discharged from the separation system is: 46 wt. % propylene, 37 wt. % C4 hydrocarbons, 4 wt. % light fractions, 2 wt. % propane and 11 wt. % hydrocarbons with 5 or more carbons.

The present invention has been described in detail as above. However, the present invention is not limited to the specific embodiments as mentioned herein. It will be understood that without departing from the scope of the present invention, any slight variations and modifications may be made by those skilled in the art. The scope of the present invention is limited by the claims as appended.

The invention claimed is:

1. A turbulent fluidized-bed reactor for preparing propylene and C4 hydrocarbons from oxygen-containing compounds, comprising:
a reactor shell, one or more reactor feed distributors, a first reactor gas-solid separator, a second reactor gas-solid separator, a reactor heat extractor, a product gas outlet and a reactor stripper, wherein the lower part of the turbulent fluidized-bed reactor is a reaction zone, the upper part of the turbulent fluidized-bed reactor is a settling zone, the one or more reactor feed distributors are disposed in the reaction zone, the reactor heat extractor is disposed in the reaction zone, the first reactor gas-solid separator and the second reactor gas-solid separator are placed in the settling zone or outside the reactor shell, the first reactor gas-solid separator is equipped with a regenerated catalyst inlet, the catalyst outlet of the first reactor gas-solid separator is located at the bottom of the reaction zone, the gas outlet of the first reactor gas-solid separator is located in the settling zone, the inlet of the second reactor gas-solid separator is located in the settling zone, the catalyst outlet of the second reactor gas-solid separator is placed in the reaction zone, the gas outlet of the second reactor gas-solid separator is connected to the product gas outlet, the reactor stripper passes through the reactor shell from outside to inside at the bottom of the turbulent fluidized-bed reactor and is opened in the reaction zone of the turbulent fluidized-bed reactor, a reactor stripping gas inlet is arranged at the bottom of the reactor stripper, and a spent catalyst outlet is arranged at the bottom of the reactor stripper.

2. The turbulent fluidized-bed reactor according to claim 1, wherein one or more reactor feed distributors are disposed in the reaction zone from bottom to top, and there are between one and ten distributions.

3. The turbulent fluidized-bed reactor according to claim 1, wherein the horizontal height of opening of the reactor stripper in the reactor shell is higher than 1/10 the height of the reaction zone.

4. The turbulent fluidized-bed reactor according to claim 1, wherein the first reactor gas-solid separator and the second reactor gas-solid separator are cyclone separators.

5. A device for preparing propylene and C4 hydrocarbons from oxygen-containing compounds, comprising the turbulent fluidized-bed reactor according to claim 1 and a fluidized-bed regenerator for regenerating a catalyst.

6. The device according to claim 5, wherein the fluidized-bed regenerator is a turbulent fluidized-bed regenerator.

7. The device according to claim 5, wherein the fluidized-bed regenerator comprises a regenerator shell, a regenerator feed distributor, a regenerator gas-solid separator, a regenerator heat extractor, a flue gas outlet and a regenerator stripper, in which the lower part of the fluidized-bed regenerator is a regeneration zone, the upper part of the fluidized-bed regenerator is a settling zone, the regenerator feed distributor is placed at the bottom of the regeneration zone, the regenerator heat extractor is placed in the regeneration zone, the regenerator gas-solid separator is placed in the settling zone or outside the regenerator shell, the inlet of the regenerator gas-solid separator is disposed in the settling zone, the catalyst outlet of the regenerator gas-solid separator is disposed in the regeneration zone, the gas outlet of the regenerator gas-solid separator is connected to the flue gas outlet, and the regenerator stripper is opened at the bottom of the regenerator shell;
the spent catalyst outlet of the reactor stripper is connected to the inlet of a inclined spent catalyst pipe, a spent catalyst sliding valve is arranged in the inclined spent catalyst pipe, the outlet of the inclined spent catalyst pipe is connected to the inlet of a spent catalyst lift pipe, the bottom of the spent catalyst lift pipe is provided with a spent catalyst lifting gas inlet, and the outlet of the spent catalyst lift pipe is connected to the settling zone of the fluidized-bed regenerator; and
the bottom of the regenerator stripper is provided with a regenerator stripping gas inlet, the bottom of the regenerator stripper is connected to the inlet of a inclined regenerated catalyst pipe, a regenerated catalyst sliding valve is arranged in the inclined regenerated catalyst pipe, the outlet of the inclined regenerated catalyst pipe is connected to the inlet of a regenerated catalyst lift pipe, the bottom of the regenerated catalyst lift pipe is provided with a regenerated catalyst lifting gas inlet, and the outlet of the regenerated catalyst lift pipe is connected to the regenerated catalyst inlet of the first reactor gas-solid separator.

8. A method for preparing propylene and C4 hydrocarbons from oxygen-containing compounds, including:
feeding a raw material containing an oxygen-containing compound from n reactor feed distributors to a reaction zone of a turbulent fluidized-bed reactor, and contacting the raw material with a catalyst, to generate a stream containing propylene and C4 hydrocarbons product and a spent catalyst containing carbon;
sending the stream discharged from the turbulent fluidized-bed reactor containing propylene and C4 hydrocarbons product into a product separation system, obtaining propylene, C4 hydrocarbons, light fractions, propane and hydrocarbons with five or more carbons after separation, wherein the light fractions contain more than 90 wt % of ethylene and a small amount of methane, ethane, hydrogen, CO and CO2, returning 70 wt. % or more of the light fractions to the reaction zone of the turbulent fluidized-bed reactor from the reactor feed distributor at the bottom-most of the turbulent fluidized-bed reactor, and reacting ethylene and the oxygen-containing compounds to perform an alkylation reaction in presence of the catalyst, to produce a product containing propylene; and regenerating the spent catalyst by a fluidized-bed regenerator, and after being gas-solid separated by a first reactor gas-solid separator, the regenerated catalyst is fed to the bottom of the reaction zone of the turbulent fluidized-bed reactor.

9. The method according to claim 8, wherein the method is carried out by using the device comprising:

a reactor shell, one or more reactor feed distributors, a first reactor gas-solid separator, a second reactor gas-solid separator, a reactor heat extractor, a product gas outlet and a reactor stripper, wherein the lower part of the turbulent fluidized-bed reactor is a reaction zone, the upper part of the turbulent fluidized-bed reactor is a settling zone, the one or more reactor feed distributors are disposed in the reaction zone, the reactor heat extractor is disposed in the reaction zone, the first reactor gas-solid separator and the second reactor gas-solid separator are placed in the settling zone or outside the reactor shell, the first reactor gas-solid separator is equipped with a regenerated catalyst inlet, the catalyst outlet of the first reactor gas-solid separator is located at the bottom of the reaction zone, the gas outlet of the first reactor gas-solid separator is located in the settling zone, the inlet of the second reactor gas-solid separator is located in the settling zone, the catalyst outlet of the second reactor gas-solid separator is placed in the reaction zone, the gas outlet of the second reactor gas-solid separator is connected to the product gas outlet, the reactor stripper passes through the reactor shell from outside to inside at the bottom of the turbulent fluidized-bed reactor and is opened in the reaction zone of the turbulent fluidized-bed reactor, a reactor stripping gas inlet is arranged at the bottom of the reactor stripper, and a spent catalyst outlet is arranged at the bottom of the reactor stripper;

the turbulent fluidized-bed reactor and a fluidized-bed regenerator for regenerating a catalyst.

10. The method according to claim 9, wherein the spent catalyst passes through the reactor stripper, the inclined spent catalyst pipe, the spent catalyst sliding valve and the spent catalyst lift pipe into the settling zone of the fluidized-bed regenerator;

a regeneration medium enters the regeneration zone of the fluidized-bed regenerator and reacts with the spent catalyst to perform calcination to produce a flue gas containing CO and CO2 and the regenerated catalyst, and the flue gas is discharged after dust removal by the regenerator gas-solid separator;

the regenerated catalyst passes through the regenerator stripper, the inclined regenerated catalyst pipe, the regenerated catalyst sliding valve and the regenerated catalyst lift pipe into the inlet of the first reactor gas-solid separator, and after gas-solid separation, the regenerated catalyst enters the bottom of the reaction zone of the turbulent fluidized-bed reactor;

a reactor stripping gas enters the reactor stripper via the reactor stripping gas inlet and contacts countercurrent with the spent catalyst, and then enters the turbulent fluidized-bed reactor; a spent catalyst lifting gas enters the spent catalyst lift pipe via the spent catalyst lifting gas inlet and contacts cocurrent with the spent catalyst, and then enters the settling zone of the fluidized-bed regenerator; and a regenerator stripping gas enters the regenerator stripper via the regenerator stripping gas inlet and contacts countercurrent with the regenerated catalyst, and then enters the fluidized-bed regenerator; a regenerated catalyst lifting gas enters the regenerated catalyst lift pipe via the regenerated catalyst lifting gas inlet and contacts cocurrent with the regenerated catalyst, and then enters the inlet of the first reactor gas-solid separator.

11. The method according to claim 8, wherein the circulating amount of the light fractions is 5-40 wt. % of the feeding amount of the oxygen-containing compound.

12. The method according to claim 8, wherein the carbon content of the spent catalyst is 5-12 wt. %, and the carbon content of the regenerated catalyst is less than 2 wt. %.

13. The method according to claim 8, wherein the oxygen-containing compound is methanol and/or dimethyl ether; and/or the regeneration medium is any one of air, oxygen-poor air or water vapor or a mixture thereof; and/or the reactor stripping gas, the regenerator stripping gas, the spent catalyst lifting gas and the regenerated catalyst lifting gas are water vapor or nitrogen.

14. The method according to claim 8, wherein the reaction conditions in the reaction zone of the turbulent fluidized-bed reactor are: the apparent linear velocity of gas is in a range from 0.1 m/s to 2 m/s, the reaction temperature is in a range from 300° C. to 550° C., the reaction pressure is in a range from 100 kPa to 500 kPa, and the bed density is in a range from 200 kg/m3 to 1200 kg/m3.

15. The method according to claim 8, wherein the reaction conditions in the regeneration zone of the fluidized-bed regenerator are: the apparent linear velocity of gas is in a range from 0.1 m/s to 2 m/s, the regeneration temperature is in a range from 500° C. to 750° C., the regeneration pressure is in a range from 100 kPa to 500 kPa, and the bed density is in a range from 200 kg/m3 to 1200 kg/m3.

16. The turbulent fluidized-bed reactor according to claim 2, wherein the horizontal height of opening of the reactor stripper in the reactor shell is higher than ⅒ the height of the reaction zone.

17. The turbulent fluidized-bed reactor according to claim 2, wherein the reactor gas-solid separator and the reactor gas-solid separator are cyclone separators.

18. A device for preparing propylene and C4 hydrocarbons from oxygen-containing compounds, comprising the turbulent fluidized-bed reactor according to claim 2 and a fluidized-bed regenerator for regenerating a catalyst.

19. A device for preparing propylene and C4 hydrocarbons from oxygen-containing compounds, comprising the turbulent fluidized-bed reactor according to claim 3 and a fluidized-bed regenerator for regenerating a catalyst.

20. The method according to claim 8, wherein the method is carried out by using a device comprising:

a reactor shell, one or more reactor feed distributors, a first reactor gas-solid separator, a second reactor gas-solid separator, a reactor heat extractor, a product gas outlet and a reactor stripper, wherein the lower part of the turbulent fluidized-bed reactor is a reaction zone, the upper part of the turbulent fluidized-bed reactor is a settling zone, the one or more reactor feed distributors are disposed in the reaction zone, the reactor heat extractor is disposed in the reaction zone, the first reactor gas-solid separator and the second reactor gas-solid separator are placed in the settling zone or outside the reactor shell, the first reactor gas-solid separator is equipped with a regenerated catalyst inlet, the catalyst outlet of the first reactor gas-solid separator is located at the bottom of the reaction zone, the gas outlet of the first reactor gas-solid separator is located in the settling zone, the inlet of the second reactor gas-solid separator is located in the settling zone, the catalyst outlet of the second reactor gas-solid separator is placed in the reaction zone, the gas outlet of the second reactor gas-solid separator is connected to the product gas outlet, the reactor stripper passes through the reactor shell from outside to inside at the bottom of the turbulent fluidized-bed reactor and is opened in the reaction zone of the turbulent fluidized-bed reactor, a reactor stripping gas inlet is arranged at the bottom of the reactor stripper, and a spent catalyst outlet is arranged at the bottom of the reactor stripper;

a reactor shell, one or more reactor feed distributors, a first reactor gas-solid separator, a second reactor gas-solid separator, a reactor heat extractor, a product gas outlet and a reactor stripper, wherein the lower part of the turbulent fluidized-bed reactor is a reaction zone, the upper part of the turbulent fluidized-bed reactor is a settling zone, the one or more reactor feed distributors are disposed in the reaction zone, the reactor heat extractor is disposed in the reaction zone, the first reactor gas-solid separator and the second reactor gas-solid separator are placed in the settling zone or outside the reactor shell, the first reactor gas-solid separator is equipped with a regenerated catalyst inlet, the catalyst outlet of the first reactor gas-solid separator is located at the bottom of the reaction zone, the gas outlet of the first reactor gas-solid separator is located in the settling zone, the inlet of the second reactor gas-solid separator is located in the settling zone, the catalyst outlet of the second reactor gas-solid separator is placed in the reaction zone, the gas outlet of the second reactor gas-solid separator is connected to the product gas outlet, the reactor stripper passes through the reactor shell from outside to inside at the bottom of the turbulent fluidized-bed reactor and is opened in the reaction zone of the turbulent fluidized-bed reactor, a reactor stripping gas inlet is arranged at the bottom of the reactor stripper, and a spent catalyst outlet is arranged at the bottom of the reactor stripper;

the turbulent fluidized-bed reactor and a fluidized-bed regenerator for regenerating a catalyst;

a regenerator shell, a regenerator feed distributor, a regenerator gas-solid separator, a regenerator heat extractor, a flue gas outlet and a regenerator stripper, in which the lower part of the fluidized-bed regenerator is a regeneration zone, the upper part of the fluidized-bed regenerator is a settling zone, the regenerator feed distributor is placed at the bottom of the regeneration zone, the regenerator heat extractor is placed in the regeneration zone, the regenerator gas-solid separator is placed in the settling zone or outside the regenerator shell, the inlet of the regenerator gas-solid separator is disposed in the settling zone, the catalyst outlet of the regenerator gas-solid separator is disposed in the regeneration zone, the gas outlet of the regenerator gas-solid separator is connected to the flue gas outlet, and the regenerator stripper is opened at the bottom of the regenerator shell;

the spent catalyst outlet of the reactor stripper is connected to the inlet of a inclined spent catalyst pipe, a spent catalyst sliding valve is arranged in the inclined spent catalyst pipe, the outlet of the inclined spent catalyst pipe is connected to the inlet of a spent catalyst lift pipe, the bottom of the spent catalyst lift pipe is provided with a spent catalyst lifting gas inlet, and the outlet of the spent catalyst lift pipe is connected to the settling zone of the fluidized-bed regenerator; and the bottom of the regenerator stripper is provided with a regenerator stripping gas inlet, the bottom of the regenerator stripper is connected to the inlet of a inclined regenerated catalyst pipe, a regenerated catalyst sliding valve is arranged in the inclined regenerated catalyst pipe, the outlet of the inclined regenerated catalyst pipe is connected to the inlet of a regenerated catalyst lift pipe, the bottom of the regenerated catalyst lift pipe is provided with a regenerated catalyst lifting gas inlet, and the outlet of the regenerated catalyst lift pipe is connected to the regenerated catalyst inlet of the first reactor gas-solid separator.

* * * * *